US005843633A

United States Patent [19]
Yin et al.

[11] Patent Number: 5,843,633
[45] Date of Patent: Dec. 1, 1998

[54] CHARACTERIZATION OF A HUMAN HEMATOPOIETIC PROGENITOR CELL ANTIGEN

[75] Inventors: Amy Yin, San Jose; Sheri Miraglia, Alameda; David W. Buck, Half Moon Bay, all of Calif.

[73] Assignee: Amcell Corporation, Sunnyvale, Calif.

[21] Appl. No.: 639,891

[22] Filed: Apr. 26, 1996

[51] Int. Cl.$^6$ .............................. C12N 5/20; C12P 21/08; C07K 16/28

[52] U.S. Cl. .............................. 435/2; 435/326; 435/346; 435/372.1; 435/7.21; 435/343; 530/388.7; 530/389.6; 530/391.3

[58] Field of Search .............................. 530/391.3, 387.1, 530/388.1, 388.7, 389.6; 435/2, 7.21, 240.2, 343, 326, 346, 372.1

[56] References Cited

U.S. PATENT DOCUMENTS

| | | |
|---|---|---|
| 4,452,773 | 6/1984 | Molday . |
| 4,714,680 | 12/1987 | Civin . |
| 5,061,620 | 10/1991 | Tsukamoto et al. . |
| 5,411,863 | 5/1995 | Miltenyi . |

FOREIGN PATENT DOCUMENTS

| | | |
|---|---|---|
| 0 662 512 A | 7/1995 | European Pat. Off. . |

OTHER PUBLICATIONS

Olweus, J. et al. Blood 84 (!0 Suppl. 1) 420A, Abstract # 1666, 1994.
Olweus, J. et al. Blood 85 (9):2402–2413, May 1, 1995.
Kato, K. et al. Cytometry 14: 384–392, Apr. 1993.
Database EMBL, entry HS057109, Accession No. R40057, May 28, 1995.
Database EMBL, entry HS499102, Accession No. R36499, May 5, 1995.
Database EMBL, entry HS59896, Accession No. R32598, May 4, 1995.
Database EMBL, entry HSGS04157, Accession No. D25789, Nov. 27, 1995.
Database EMBL, entry HSHBC4137, Accession No. D82259, Feb. 9, 1996.
Database EMBL, entry HSW25808, Accession No. W25808, May 10, 1996.
Sutherland and Keating, "The CD34 Antigen: Structure, Biology, and Potential Clinical Applications," J. of Hematotherapy (1992), 1:115–129.
Civin and Gore, "Antigenic Analysis of Hematopoiesis: A Review," J. of Hematotherapy (1993), 2:137–144.
"Purification of CD34 Positive Cells from Human Bone Marrow Using High Gradient Magnetic Separation", Terry E. Thomas and Peter M. Lansdorp, Advances in Bone Marrow Purging and Processing, pp. 537–544, 1992.
"Rapid Positive Selection of CD34 + Cells Using Magnetic Microspheres Coated with Monoclonal Antibody QBEND/10 Linked via a Cleavable Disulphide Bond", Philip G. Grimsley, T. Andrew S. Amos, Myrtle Y. Gordon, Melvyn F. Greaves, 1993, pp. 898–908.
"High Gradient Magnetic Cell Separation With MACS", Stefan Miltenyi, Werner Muller, Walter Weichel, Andreas Radbruch, 1990, pp. 231–238.
"Detection of a Human CFC With High Proliferative Potential", I.K. McNiece, F.M. Stewart, D.M. Deacon, D.S. Temeles, K.M. Zsebo, S.C. Clark, P.J. Quesenberry, Blood, vol. 74, No. 2, Aug. 1, 1989, pp. 609–612.
"Characterization of Stroma–Dependent Blast Colony–Forming Cells in Human Marrow", M.Y. Gordon, C.R. Dowding, G.P. Riley, M.F. Greaves, Journal of Cellular Physiology, 1987, pp. 150–156.
"Resting and activated subsets of mouse multipotent hematopoietic stem cells", Garald J. Spangrude, Gregory R. Johnson, Jun. 18, 1990, pp. 7433–7439.
"Cytokine–dependent Long–Term Culture of Highly Enriched Precursors of Hematopoietic Progenitor Cells from Human Bone Marrow", John Brandt, Edward F. Srour, Koen van Besien, Robert A. Briddell, Ronald Hoffman, The American Society for Clinical Incvestigation, Inc., Sep. 1990, pp. 932–941.
Establishment of a Clinical Threshold Cell Dose: Correlation Between CFU–GM and Duration of Aplasia, L.B. To, M.M. Roberts C.M. Rawling, P.A. Rowlings, P.G. Dyson, T.P. Rawling, D.N. Haylock, C.A. Juttner, in Hematopietic Stem Cells, Wonder et al., Eds., 1993, AlphaMed Press, pp. 15–20.
"Novel B219/OB receptor isoforms: Possible role of leptin in hematopoiesis and reproduction", Joseph A. Cioffi, Alan W. Shafer, Thomas J. Zupancic, Julie Smith–Gbur, Adel Mikhail, Doros Platika and H. Ralph Snodgrass, Nature Medicine, vol. 2, No. 5, May 1996, pp. 585–589.
Identification of a Novel DNA Sequence Differentially Expressed between Normal Human CD34+CD38$^{hi}$ and CD34+CD38$^{lo}$ Marrow Cells, Lynn Graf and Beverly Torok–Storb, Blood, vol. 86, No. 2 Jul. 15, 1995, pp. 548–556.
Ontogeny of Hematopoietic Stem Cell Development: Reciprocal Expression of CD33 and a Novel Molecule by Maturing Myeloid and Erythroid Progenitors, Carolyn Brashem–Stein, David A. Flowers, Franklin O. Smith, Steven J. Staats, Robert G. Andrews, Irwin D. Bernstein, Blood, vol. 82, No. 3 Aug. 1, 1993, pp. 792–799.

(List continued on next page.)

*Primary Examiner*—Frank C. Eisenschenk
*Assistant Examiner*—Evelyn Rabin
*Attorney, Agent, or Firm*—Cooley Godward LLP

[57] ABSTRACT

An hematopoietic progenitor cell antigen, and antibodies that specifically bind to the antigen are provided. Expression of the antigen is highly tissue specific. It is only detected on a subset of hematopoietic progenitor cells derived from human bone marrow, fetal bone marrow and liver, cord blood and adult peripheral blood. The subset of cells recognized by AC133 is CD34$^{bright}$, and contains substantially all of the CFU-GM activity present in the CD34$^+$ population. This highly specific distribution of AC133 makes it exceptionally useful as a reagent for isolating and characterizing human hematopoietic progenitor and stem cells. Cells selected for expression of AC133 antigen may be further purified by selection for other hematopoietic stem cell and progenitor cell markers.

12 Claims, 9 Drawing Sheets

OTHER PUBLICATIONS

"A Hematopoietic Organ–Specific 49–kD Nuclear Antigen: Predominance in Immature Normal and Tumor Granulocytes and Detection in Hematopoietic Precursor Cells", By Byeong–Chel Lee, Yaron Shav–Tal, Amnon Peled, Yael Gothelf, Wen Jiang, Jeki Toledo, Rob E. Ploemacher, Nehama Haran–Ghera, Dov Zipori, Blood, vol. 87, No. 6, Mar. 15, 1996, pp. 2283–2291.

Distribution of Receptors for Granulocyte–Macrophage Colony–Stimulating Factor on Immature CD34+ Bone Marrow Cells, Differentiating Monomyeloid Progenitors, and Mature Blood Cell Subsets, A.W. Wognum, Y. Westerman, T.P. Visser, and G. Wagemaker, Blood, vol. 84, No. 3 Aug. 1, 1994, pp. 764–774.

"Characterization of hemopoietic cell populations from human cord blood expressing c–kit", G. Reisbach, I. Bartke, B. Kempkes, G. Kostka, J. Ellwart, A. Birner, K. Thalmeier, R. Mailhammer, G.W. Bornkamm, A. Ullrich, P. Dormer, 1993 International Society for Experimental Hematology, pp. 74–79.

"Identification of homeobox genes expressed in human haemopoietic progenitor cells", Paul Moretti, Paul Simmons, Paul Thomas, David Haylock, Peter Rathjen, Matthew Vadas and Richard D'Andrea, 1994 Elsevier Science B.V., pp. 213–219.

"Development of a Large–Scale Immunomagnetic Separation System for Harvesting CD34–Positive Cells From Bone Marrow", A. Hardwick, P. Law, V. Mansour, D. Kulcinski, L. Ishizawa and A. Gee, Advances in Bone Marrow Purging and Processing, 1992, pp. 583–589.

"Monitoring of Kinetics of CD34 Positive Cells By Immunomagnetic Beads During Peripheral Blood Stem Cell Harvest for Autotransplantation", Naritoshi Oku, Chihiro Shimazaki, Eishi Ashihara, Katsunori Ohkawa, Hideo Gotoh, Tohru Inaba, Satoshi Murakami, Kunihiko Itoh, Naohisa Fujita, Hajime Tsuji and Masao Nakagawa, Advances in Bone Marrow Purging and Processing, 1992, pp. 553–560.

"CD34 Positive Cell Selection By Immunomagnetic Techniques", A. Bigas, B. Amill, C. Canals, D. Tugues and J. Garcia, Advances in Bone Marrow Purging and Processing, pp. 545–551, 1992.

CHARACTERIZATION OF A HUMAN HEMATOPOIETIC PROGENITOR CELL ANTIGEN

TECHNICAL FIELD

The field of this invention is antigens expressed by hematopoietic progenitor cells.

BACKGROUND

The high turnover of mammalian blood cells requires a supply of hematopoietic stem cells, which are able to give rise to other blood cell lineages. The immediate progeny of the hematopoietic stem cell is believed to be "progenitor" cells, which are capable of giving rise to various cell types within one or more lineages, i.e. the erythroid, myeloid and lymphoid lineages. The stem cell and progenitor cell populations constitute only a small percentage of the total number of cells in bone marrow, fetal liver, etc. These populations are of immense interest because of their ability to repopulate the hematopoietic system.

A number of methods have been described in the literature for the purification or enrichment of hematopoietic progenitor cell populations. There is significant commercial interest in these methods because hematopoietic progenitors have a number of clinical uses. Progenitor cell transplantation is currently used in conjunction with chemotherapy and radiation for the treatment of leukemia, breast cancer and other tumors. Frequently, autologous transplants are used to avoid the danger of graft rejection, but there is an increased risk of disease reappearance, due to the presence of tumor cells in the engrafting cell population. Transplantation of a more purified source of progenitor cells is therefore preferable.

There is also interest in the use of hematopoietic progenitor cells as a vehicle for gene therapy. Although not yet proven in the clinic, the longevity of hematopoietic stem cells, and the dissemination of their progeny in the vasculature, are desirable characteristics. A number of vectors have been described, including several retrovirus and adenovirus based constructs, that can transfect hematopoietic stem cells.

Proteins and other cell surface markers found on hematopoietic stem cell and progenitor cell populations are of great interest. They are useful in preparing reagents for the separation and isolation of these populations, and in the further characterization of these important cells.

RELEVANT LITERATURE

U.S. Pat. No. 5,061,620 describes a substantially homogeneous human hematopoietic stem cell composition and the manner of obtaining such composition. Stromal cell-associated hematopoiesis is described by Paul et al. (1991) *Blood* 77:1723–1733. The phenotype of stem cells with rhodamine staining is discussed in Spangrude and Johnson (1990) *P.N.A.S.* 87:7433–7437. Cell surface antigen expression in hematopoiesis is discussed in Strauss et al. (1983) *Blood* 61:1222–1231 and Sieff et al. (1982) *Blood* 60:703–713. Descriptions of pluripotential hematopoietic cells are found in McNiece et al. (1989) *Blood* 74:609–612 and Moore et al. (1979) *Blood Cells* 5:297–311. Characterization of a human hematopoietic progenitor cell capable of forming blast cell-containing colonies in vitro is found in Gordon et al. (1987) *J. Cell. Physiol.* 130:150–156 and Brandt et al. (1988) *J. Clin. Invest.* 82:1017–1027. The use of progenitor cells in transplantation is discussed in To et al. in *Progenitor Threshold in Transplantation* (ISBN 1-880854 17-1) pp. 15–20.

The use of high gradient magnetic separation for the isolation of human hematopoietic progenitor cells is described in Thomas and Landsdorp (1992) in *Advances in Bone Marrow Purging* pp.537–544; and Kato and Radbruch (1993) *Cytometry* 14:384–392. Other methods of magnetic selection for human hematopoietic progenitor cells are described in Bigas et al. (1992) in *Advances in Bone Marrow Purging* pp.545–551; Oku et al. (1992) in *Advances in Bone Marrow Purging* pp.553–560; and Hardwick et al. (1992) in *Advances in Bone Marrow Purging* pp.583–589. High gradient magnetic cell sorting is described in Miltenyi et al. (1990) *Cytometry* 11:231–238. Molday, U.S. Pat. No. 4,452,773 describes the preparation of magnetic iron-dextran microspheres and provides a summary describing the various means of preparation of particles suitable for attachment to biological materials.

SUMMARY OF THE INVENTION

Methods and compositions are provided for the enrichment and characterization of human hematopoietic progenitor and stem cells. Novel antigen and antibody compositions are provided for use in the subject methods, and for the further investigation of hematopoietic progenitor cell biology. The hematopoietic cells may be obtained from various sources, including fetal and adult bone marrow, cytokine mobilized peripheral blood cells and fetal liver. The progenitor cells are identified or selected through the use of reagents that specifically bind to the AC133 antigen, e.g. AC133 monoclonal antibody.

BRIEF DESCRIPTION OF THE DRAWINGS

In FIG. 5A the x axis represents CD38-FITC staining, and the y axis represents HPCA2-PE staining. In FIGS. 5B, 5C and 5D, the x axis represents staining with HPCA2-FITC. The y axis in FIG. 5B represents cell staining with anti-HLA-DR-PE. The y axis in FIG. 5C represents cell staining with anti-CDw90-PE. The y axis in FIG. 5D represents cell staining with anti-CD117-PE. The numbers represent the percent of total cells that fall within the boxed gates.

DESCRIPTION OF THE SPECIFIC EMBODIMENTS

Methods and compositions are provided for the enrichment and/or characterization of human hematopoietic stem cells or progenitor cells. The immediate progeny of the hematopoietic stem cell is believed to be "progenitor" cells, which are capable of giving rise to various cell types within one or more lineages. The stem or progenitor cells are identified or selected through the use of novel reagents that specifically bind to the AC133 antigen (Ag), e.g. AC133 monoclonal antibody. The high tissue specificity of AC133 expression is particularly advantageous during enrichment for highly purified progenitor cell populations. The AC133 positive cell population is highly enriched for cells that are active in assays measuring progenitor cell activity, particularly in the CFU-GM activity. The subset of cells that is AC133 negative and CD34 positive is enriched for BFU-E activity, a measure of erythroid committed progenitor cell activity.

A monoclonal antibody is provided, AC133, with specificity for a novel stem cell antigen expressed on a subset of hematopoietic progenitor cells derived from human bone marrow, fetal bone marrow and liver, cord blood and adult peripheral blood. The subset of progenitor cells recognized by AC133 are $CD34^{bright}$, and contain substantially all of the CFU-GM activity present in the $CD34^+$ subset. For purposes of transplantation, cells active in CFU-GM are of particular interest because they provide for production of neutrophils. AC133 antibody provides a means for the positive immunoselection of hematopoietic progenitor cell populations, as well as the phenotypic analysis of progenitor cell populations using flow cytometry. Cells selected for expression of AC133 antigen may be further purified by selection for other hematopoietic stem cell and progenitor cell markers.

Molecules of interest in the subject methods are the AC133 antigen, antibodies that specifically bind to AC133, and nucleic acid sequences encoding the AC133 antigen. The antigen may be isolated from natural sources, or produced using recombinant DNA technology. The nucleic acids may be cDNA, a genomic sequence, or a synthetic sequence, comprising the coding sequence by itself or in conjunction with transcriptional regulatory regions, and the like. The AC133Ag is obtained in a purified form by isolation from cells, which may be identified as positive by AC133 antibody binding, through various affinity binding methods known in the art. Antibodies are of particular interest. Antibodies to AC133 Ag are obtained by immunizing a xenogeneic immunocompetent mammalian host, including murine, rodentia, lagomorpha, ovine, porcine, bovine, etc. with human hematopoietic progenitor cells. The choice of a particular host is primarily one of convenience.

A suitable progenitor cell population for immunization is obtained by isolating $CD34^+$ cells from cytokine mobilized peripheral blood, bone marrow, fetal liver, etc. The cells may be stimulated with phytohemagglutinin prior to their use as an immunogen.

Immunizations are performed in accordance with conventional techniques, where the cells may be injected subcutaneously, intramuscularly, intraperitoneally, intravascularly, etc. Normally, from about $10^6$ to $10^8$ cells will be used, which may be divided up into 1 or more injections, usually not more than about 8 injections, over a period of from about one to three weeks. The injections may be with or without adjuvant, e.g. complete or incomplete Freund's adjuvant, specol, alum, etc.

In a preferred embodiment, contralateral immunization is used, as described in the examples. This method relies on the trafficking ability of immune lymphocytes to home to the site of antigen stimulation. The animals are pre-immunized at a localized site on one side of the body, such as the left footpad, with cells that express many immunodominant but irrelevant antigens. Various mature hematopoietic cells may be used for this purpose. The immunogen of interest is injected at a localized site on the opposite side of the animal. Lymphocytes pre-immunized with and responding to irrelevant antigens are decoyed to the left hand draining lymph nodes, while the lymphocytes responding to the immunogen of interest will be present in the right hand draining lymph nodes, e.g. the popliteal lymph nodes for footpad injection. This popliteal lymph node is used as a source of cells for fusion.

After completion of the immunization schedule, the antiserum may be harvested in accordance with conventional ways to provide polygonal antisera specific for the surface membrane proteins of hematopoietic progenitor cells, including the AC133 Ag. Lymphocytes are harvested from the appropriate lymphoid tisue, e.g. spleen, draining lymph node, etc., and fused with an appropriate fusion partner, usually a myeloma line, producing a hybridoma secreting a specific monoclonal antibody. Screening clones of hybridomas for the antigenic specificity of interest is performed in accordance with conventional methods.

Of particular interest is the monoclonal antibody AC133 described in the Experimental section, antibodies that bind to the AC133 antigen, cross-reactive antibodies, i.e. those which bind to the same epitope, and substantially inhibit simultaneous binding, species analogs thereof, binding fragments thereof, and conjugates thereof. A deposit of the murine hybridoma cell line AC133 was made at the American Type Tissue Collection, 12301 Parklawn Drive, Rockville Md. 20852, on Apr. 24, 1997, and given the ATCC designation HB12346. These antibodies are capable of immunoselection for the hematopoietic subset of interest.

The subject antibodies may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework residues with the corresponding human sequence (see WO 92/02190).

The use of Ig cDNA for construction of chimeric immunoglobulin genes is known in the art (Liu et al. (1987) P.N.A.S. 84:3439 and (1987) J. Immunol. 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

AC133 antibody is characterized by binding to a protein under Western blot conditions from reducing SDS-PAGE gels that has a molecular weight, based on commercially available standards, in the range of about 125 to 127 kD. The antibody recognizes a protein determinant, evidenced by its binding to tunicamycin or neuraminidase treated antigen. The AC133 antigen is expressed on a subset of CD34$^+$ cells, but is absent on endothelium and fibroblasts. Included in the population of AC133 positive cells are HLA-DR$^+$, CDw90$^+$ and CD117$^+$ progenitor cells. This population contains substantially all of the hematopoietic stem activity present in the CD34$^+$ subset of hematopoietic cells.

The subject antibodies have a number of in vivo and in vitro uses. Immunoselection with AC133 provides a means of purifying hematopoietic progenitor and stem cells. The antibodies find use in diagnostics to detect or enumerate hematopoietic progenitor cells, dividing the CD34 positive population into functionally distinct sub-populations, isolation of progenitor cells, preparation of progenitors to produce mature blood cells, etc. Biological samples, e.g. blood or derivatives thereof, biopsies, synovial fluid, etc. are assayed by any convenient immunoassay method for the presence of cells expressing the surface molecule bound by the subject antibodies. Assays may be performed on cell lysates, intact cells, frozen sections, etc.

The subject antibodies are useful for the preparation of substantially pure human hematopoietic progenitor and stem cells. A subset of progenitor cells is separated from other hematopoietic cells on the basis of AC133 binding, and may be further separated by binding to other surface markers known in the art. The source of hematopoietic cells may be fetal or adult bone marrow, fetal liver, umbilical cord blood, peripheral blood, particularly cytokine mobilized peripheral blood (see, for example, Campos et al. (1993) *Leukemia* 7:1409–15 and Grigg et al. (1993) Bone Marrow Transplant 11, Suppl 2:23–9), and the like.

Human stem cells have been reported to have the phenotype CD34$^{bright}$; HLA-DR$^+$; CD38$^{dim/negative}$; CD117(c-kit)$^{dim}$; CDw90(Thy-1)$^+$; and to lack expression of a variety of lineage specific markers, including CD3, CD4, CD7, CD8, CD14 and CD15. A negative designation indicates that the level of staining is at or below the brightness of an isotype matched negative control. A dim designation indicates that the level of staining may be near the level of a negative stain, but may also be brighter than an isotype matched control.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide, LDS). Red blood cells may be removed by elutriation, hemolysis, Ficoll-Paque gradients, etc. Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. AC133$^+$, CDw90$^+$ or CD117$^+$; AC133$^-$, CD34$^+$, etc. Fluorochromes which find use in a multi-color analysis include phycobiliproteins, e.g. phycoerythrin and allophycocyanins; fluorescein and Texas red.

In one embodiment of the subject invention the AC133 antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyidithio) propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, AC133 antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

The antibody is added to a hematopoietic cell sample. The amount of AC133 Ab necessary to bind a particular cell subset is empirically determined by performing a test separation and analysis. The cells and AC133 Ab are incubated for a period of time sufficient for complexes to form, usually at least about five minutes, more usually at least about 10 minutes, and usually not more than one hour, more usually not more than about 30 minutes.

The cells may additionally be incubated with antibodies or binding molecules specific for cell surface markers known to be present or absent on hematopoietic progenitor or stem cells. For example, CDw90, CD117 and HLA-DR are useful in the positive selection of stem cells. Various markers known to be absent on stem cells, such as CD3, CD4, CD8, CD14, CD15, etc. may be used for negative selection.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO/90/07380, PCT/US96/00953 and EP 438,520, herein incorporated by reference.

The purified cell population may be collected in any appropriate medium. Various media are commercially available and may be used, including Dulbecco's Modified Eagle Medium (dMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc.

Compositions highly enriched for human hematopoietic progenitor or stem cells are achieved in this manner. The desired cells will be at or about 80% or more of the cell composition, and preferably be at or about 90% or more of the cell composition. Specific populations of interest include $AC133^+$ cells, which are characterized as $CD34^{bright}$ and $HLA-DR^+$. This population may be further selected for those cells that are $CDw90^+$, $CD117^+$ and/or $CD38^{dim}$. Functionally these cells are highly enriched for CFU-GM activity. Another population of interest is $CD133^-$ and $CD34^+$, which is enriched for BFU-e activity. The use of the subject antibodies for purification are advantageous over the use of CD34, because AC133 is expressed by a more restricted population of cells, thereby permitting a more enriched subset for the specific activity of interest.

Once the desired cells have been isolated, they may be propagated by growing in conditioned medium from stromal cells, coculturing with such stromal cells, or in medium comprising maintenance factors supporting the proliferation of such progenitor cells, e.g. stem cell factor, combinations of interleukins, etc. The medium employed for culturing cells is conveniently a defined enriched medium, such as IMDM or a mixture of IMDM and RPMI, and will generally be composed of salts, amino acids, vitamins, $5 \times 10^{-5}$ M β-mercaptoethanol, streptomycin/penicillin and 10% fetal calf serum, and may be changed from time to time, generally at least once to twice per week.

The subject cell compositions may find use in a variety of ways. They can be used to reconstitute an irradiated host and/or a host subject to chemotherapy. By providing for maturation, proliferation and differentiation into one or more selected lineages through specific different growth factors the progenitor cells may be used as a source of committed cells. Such factors as erythropoietin, colony stimulating factors, e.g. GM-CSF, G-CSF or M-CSF, interleukins e.g. IL-1, -2, -3, -4, -5, -6, -7, -8, -9, -10, etc., or the like, or stromal cells may be used to influence the growth and differentiation of progenitor cells.

The cells may also be used in the isolation and evaluation of factors associated with the differentiation and maturation of hematopoietic cells. Thus, the cells may be used in assays to determine the activity of media, such as conditioned media, evaluate fluids for growth factor activity, involvement with dedication of lineages, or the like.

The cells may be used for the treatment of genetic diseases. Genetic diseases associated with hematopoietic cells may be treated by genetic modification of autologous or allogeneic stem cells to correct a genetic defect or treat to protect against disease, e.g. HIV. For example, diseases such as β-thalassemia, sickle cell anemia, adenosine deaminase deficiency, recombinase deficiency, recombinase regulatory gene deficiency, etc. may be corrected by introduction of the wild-type gene into the subject cells, either by homologous or random recombination. Alternatively, normal allogeneic progenitor cells may be transplanted. Diseases other than those associated with hematopoietic cells may also be treated, where the disease is related to the lack of a particular secreted product such as hormone, enzyme, interferon, factor, or the like.

The cells may be frozen at liquid nitrogen temperatures and stored for long periods of time, being thawed and capable of being reused. The cells will usually be stored in 5% DMSO and 95% fetal calf serum. Once thawed, the cells may be expanded by use of growth factors or stromal cells associated with stem cell proliferation and differentiation.

The AC133 antigen may be obtained in substantially pure form from either natural sources or by recombinant techniques. From natural sources, the subset of hematopoietic progenitor cells is lysed and passed through an affinity column of AC133 monoclonal antibody. Hematopoietic progenitor cells are isolated from natural sources by conventional separation techniques, or cell lines described in the experimental section may be used as a source of antigen. The protein is eluted from the affinity column with an appropriate salt solution or aqueous/organic gradient, e.g., acetonitrile, ethanol, etc., usually in the presence of a low acid concentration, 0.1–1 percent trifluoroacetic acid. The eluted protein is then further purified by chromatography, electrophoresis, or the like in accordance with conventional ways.

Alternatively, the AC133 antigen can be obtained by recombinant techniques. Total RNA is isolated from cells that have been shown by antibody binding to express the targeted protein. Residual DNA is removed in accordance with conventional techniques and the polyadenylated RNA purified further, on oligo-dT sepharose, gel chromatography, etc. cDNA is then prepared in accordance with conventional techniques using reverse transcriptase (see Sambrook, et al., supra). The cDNA is then introduced into an appropriate cloning system, such as λgt11, where the cDNA is expressed. The phage plaques are then screened using the subject antibodies, or by employing polyclonal antisera. The cDNA inserts are then subcloned into other vectors, as desired. The cDNA may be used for further probing of the cDNA library for a complete transcript. Alternatively, the cDNA sequence may be used to probe a genomic library to identify the genomic gene encoding the subject proteins (See, for example, Molecular Cloning: A Laboratory Manual, 2nd ed., J. Sambrook, E. F. Fritsch, T. Maniatis, CSHL, Cold Spring Harbor, NY, 1989).

The subject DNA shall be intended to include the nucleotide sequences encoding the specific protein, as well as adjacent 5' and 3' non-coding nucleotide sequences involved in the regulation of expression of the protein encoded by the genes, and will include up to about the length of the mature mRNA. Also included is the corresponding genomic sequence, including introns. These non-coding sequences include terminator and polyadenylation sequences, regulatory protein binding sequences, transcriptional sequences, and the like.

The nucleic acid compositions of the subject invention may be genomic or cDNA sequences encoding all or a part of the subject protein. Fragments may be obtained of the cDNA or genomic sequence by chemically synthesizing oligonucleotides in accordance with conventional methods, by restriction enzyme digestion, by PCR amplification, etc. For the most part, fragments will be of at least 12 nt, more usually at least 18 nt. Preferably fragments will include a functional epitope. The sequence providing for a functional epitope can be determined by expression of the sequence, and assaying for reactivity of the expression product with specific antibodies by conventional immunoassay.

The DNA sequences may be obtained in substantial purity, and will be obtained as a sequence other than a sequence of an intact chromosome. Usually the DNA will be obtained substantially free of other nucleic acid compounds, generally being at least about 50%, usually at least about 90% pure and are typically "recombinant", i.e. flanked by one or more nucleotides with which they are not normally associated with on a natural chromosome.

The DNA sequences are used in a variety of ways. They may be used as probes for identifying related surface proteins in the same, or other species. The DNA may also be used to identify cells or organs that are expressing the subject genes. The manner in which one probes cells for the presence of particular nucleotide sequences, particularly as DNA, mRNA or cDNA, is well-established in the literature and does not require elaboration here. Conveniently, mRNA may be isolated free of DNA, and by using reverse transcriptase and PCR with specific primers, the subject cDNAs of interest of may be expanded, separated on gel electrophoresis and then probed using Southern blotting or sequencing. Other techniques may also find use.

Homologous sequences are those with substantial sequence similarity to AC133Ag sequences included within the subject invention, i.e. at least 80%, preferably at least 90%, more preferably at least 95% sequence identity with the nucleotide sequence of the subject DNA sequence. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Such homologous nucleic acid sequences will be detected by hybridization under low stringency conditions, for example, at 50° C. and 10XSSC (0.9M NaCl/0.09 M sodium citrate) and remain bound when subject to washing at 55° C. with 1XSSC.

For expression, the DNA sequences may be inserted into an appropriate expression vector, where the native transcriptional initiation region may be employed or an exogenous transcriptional initiation region. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly *E. coli, B. subtilis*, mammalian cells, such as CHO cells, COS cells, monkey kidney cells, lymphoid cells, particularly human cell lines, and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible.

Expression vectors for the production of fusion proteins, where the exogenous fusion peptide provides additional functionality, i.e. increased protein synthesis, stability, reactivity with defined antisera, an enzyme marker, e.g. β-galactosidase, etc., are of particular interest.

Expression cassettes may be prepared comprising the transcription initiation region, which may be constitutive or inducible, with or without an enhancer sequence, including the endogenous or heterologous enhancer sequence, the AC133 gene or fragment thereof, and a transcriptional termination region, optionally having a signal for attachment of a poly A sequence. The gene may be genomic, including the native introns, or cDNA gene, or portion thereof. Of particular interest is the use of sequences which allow for the expression of functional epitopes, usually at least about 24 nucleotides in length, more usually at least about 48 nucleotides in length, and up to the complete open reading frame of the gene.

After introduction of the DNA, the cells containing the construct may be selected by means of a selectable marker, the cells expanded and then used for expression. Where secretion is desired, a signal peptide may be joined to the sequence encoding the subject proteins or fragments thereof, whereby the protein will be expressed, translocated through the cell membrane, and processed to remove the signal peptide.

The expression cassettes may be introduced into a variety of vectors, where the vectors will normally be characterized by the ability to provide selection of cells comprising the expression vectors. The vectors may provide for extrachromosomal maintenance, particularly as plasmids in bacteria or viruses in eukaryotic cells, or for integration, particularly in mammalian cells. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker which is chosen will be selected in accordance with the nature of the host, where in some cases, complementation may be employed with auxotrophic hosts, e.g. yeast. Introduction of the DNA construct may be by any convenient means, e.g. calcium-precipitated DNA, electroporation, fusion, transfection, infection with viral vectors, etc. The following examples are offered by way of illustration and not by way of limitation.

EXPERIMENTAL

Example 1

Generation of the AC133 Monoclonal Antibody by Contralateral Immunization

Five New Zealand Black (NZB) mice were inoculated a total of seven times over a twenty day period, via the footpad route, with purified CD34 positive human progenitor cells, which had been pre-incubated with phytohemagglutinin (PHA) (Gibco/BRL).

Mice were pre-immunized on Day −3 in the left hand footpad with cells that express many immunodominant but irrelevant antigens. In this case peripheral blood mononuclear cells (PBMC) were used as an irrelevant cell, as they express many antigens such as Class I HLA antigens, HLA-DR, CD15, CD26, CD29, CD31, CD36, CD44, CD45, CD58, etc., which are also expressed on hematopoietic stem cells. On day 0 PBMC are reinjected into the left footpad, and purified stem cells are injected into the right hand footpad. PBMC and purified stem cells are pre-incubated with PHA for ten minutes and washed with PBS prior to injection. Progenitor cells were isolated from a leukaphoresis pack of a cytokine mobilized donor using immunomagnetic beads. This treatment provides non-specific adjuvant effects, and obviates the need adjuvants such as Freund's. Mice are given 5–8 such injections every three days.

Figure 1:
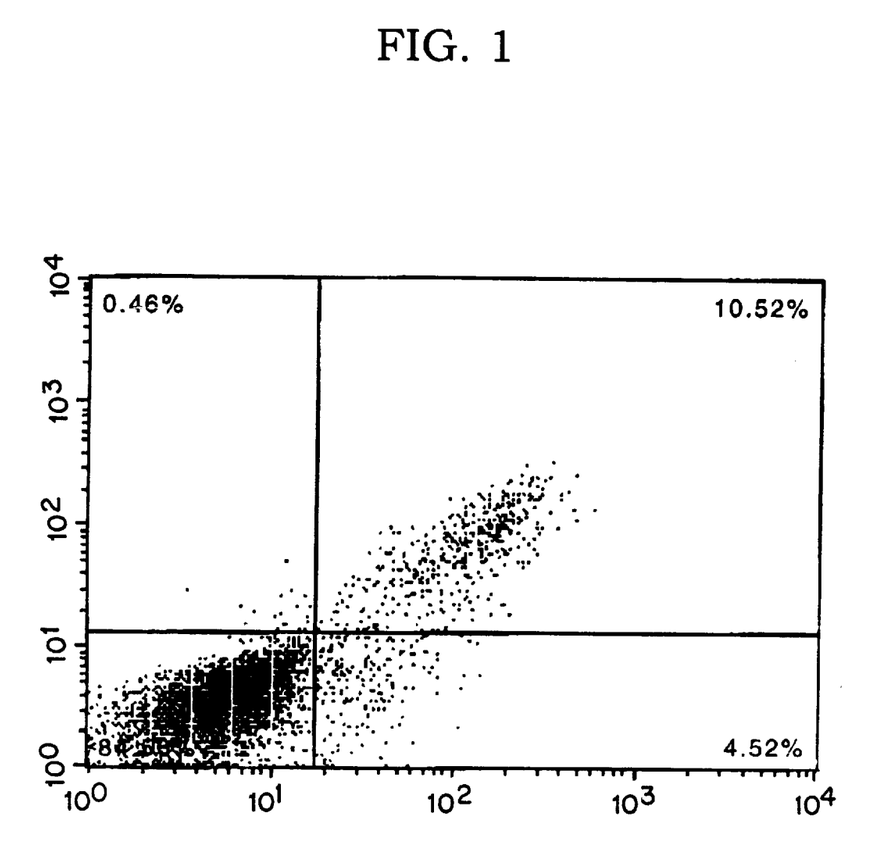
FIG. 1 shows a dot-plot from fluorescence activated cell sorting (FACS) analysis of fetal liver cells. The x axis represents cell staining for AC101 (anti-CD34) antibody conjugated to fluorescein isothiocyanate (FITC). The y axis represents cell staining with AC133 antibody conjugated to phycoerythrin (PE). The cells were counterstained with HPCA2-FITC (anti-CD34). The numbers represent the percent of total cells that fall within the boxed gates.

On day 21, one day after the last injection, the mouse right hand popliteal lymph nodes were removed. A lymphocyte suspension was prepared, and the cells fused to SP2/0 Ag14 myeloma cells using a modification of the method originally described by Kohler and Milstein (1975) *Nature* 256:495–497. Cells were plated on 96 well plates in DMEM +20% fetal calf serum, with $10^{-4}M$ hypoxanthine and 2 μg/ml azaserine (Buck et al. (1984) in *Monoclonal Antibodies and Functional Cell Lines* Kennet et al. eds., Plenum Press, New York pp.275–309). On day 10, visible hybridoma colonies were apparent. Supernatants (s/n) from hybridoma containing wells were screened for binding to a fetal liver cell preparation containing up to 15% $CD34^+$ cells, using a 2 color flow cytometry assay. Binding of mouse Ig containing s/n to the test cells was traced with rat anti-mouse Ig-conjugated to phycoerythrin (IgPE) and counterstained with a known mouse anti-CD34 antibody (AC101) conjugate. FIG. 1 shows the results from this two color FACS analysis using AC133 supernatant. AC133 is shown to stain only the bright CD34 positive cells in the fetal liver preparation. AC133 hybridoma cells were shown to secrete an IgG1/kappa antibody. The cells were expanded in culture and stocks frozen in liquid nitrogen. AC133 cells were subcloned by limiting dilution analysis and a series of positively secreting subclones were also frozen in liquid nitrogen.

Antibody Purification and Conjugation

AC133 cells were initially grown as an ascites tumor in nude mice, with collection of antibody-rich ascites fluid. More recently AC133 cells have been grown to very high density in a hollow fiber culture device (Cellmax QUAD artificial capillary system, Cellco Inc., Germantown, Md.). Pure IgG antibody was prepared from hollow fiber cultures or from ascites fluid by Protein A chromatography. Pure antibody was stored in 0.01M phosphate buffered saline (PBS) with 0.01% sodium azide at 4° C. This pure antibody stock was used to prepare fluorescein isothiocyanate (FITC) (Wofsy et al. (1980) in *Selected Methods in Cellular Immunology*. Mishell and Shiigi eds., W. H. Freeman and Co., San Francisco. pp.294–295), phycoerythrin (PE) (Hardy (1986) in *Handbook of Experimental Immunology*. Weir et al., eds. Blackwell Scientific Press, Oxford. p.31), or magnetic bead conjugates, according to standard protocols.

AC133 Expression on Normal Tissues and Cell Lines

Using standard FACS staining procedures, there was no detectable staining of peripheral blood mononuclear cells, granulocytes or platelets, or human umbilical vein endothelial cells with AC133 antibody. Examination of a panel of human cell lines by FACS analysis (data shown in Table 1) showed that only one cell line tested, the retinoblastoma cell line Y79.1, expresses detectable levels of AC133 antigen.

TABLE 1

AC133 Expression on Human Cell Lines

| Cell Line | Cell Type | AC133 |
| --- | --- | --- |
| 8402 | T cell line ($CD34^+$) | – |
| 8866 | B-LCL | – |
| AZ676 | breast carcinosarcoma | – |

TABLE 1-continued

AC133 Expression on Human Cell Lines

| Cell Line | Cell Type | AC133 |
| --- | --- | --- |
| BJAB | N. American Burkitts' lymphoma | – |
| BT474 | breast tumor | – |
| BT549 | breast tumor | – |
| BT20 | breast tumor | – |
| CaCL74-36 | melanoma | – |
| Daudi | B-LCL | – |
| Du4475 | breast tumor ($CD34^+$) | – |
| HEL92.1.7 | erythroleukemia | – |
| HL-60 | promyelocytic leukemia | – |
| HPB-ALL | acute lymphocytic leukemia | – |
| HS-R | myeloma ($EBV^+$) | – |
| HT1080 | fibrosarcoma | – |
| HT29 | colon adenocarcinoma | – |
| IM-9 | B-LCL | – |
| JM | T cell line | – |
| Jurkat | T cell line | – |
| KG1a | acute myelogenous leukemia ($CD34^+$) | – |
| KG1 | acute myelogenous leukemia ($CD34^+$) | – |
| KG1a.5 | acute myelogenous leukemia ($CD34^+$) | – |
| K562 | erythroleukemia | – |
| MOLT-4 | T cell line | – |
| MCF-7 | breast tumor | – |
| Raji | B-LCL | – |
| RPMI 8226 | myeloma | – |
| SK HEP-1 | hepatoma | – |
| U937 | histiocytic lymphoma | – |
| Y79.1 | retinoblastoma | + |

Figure 2:
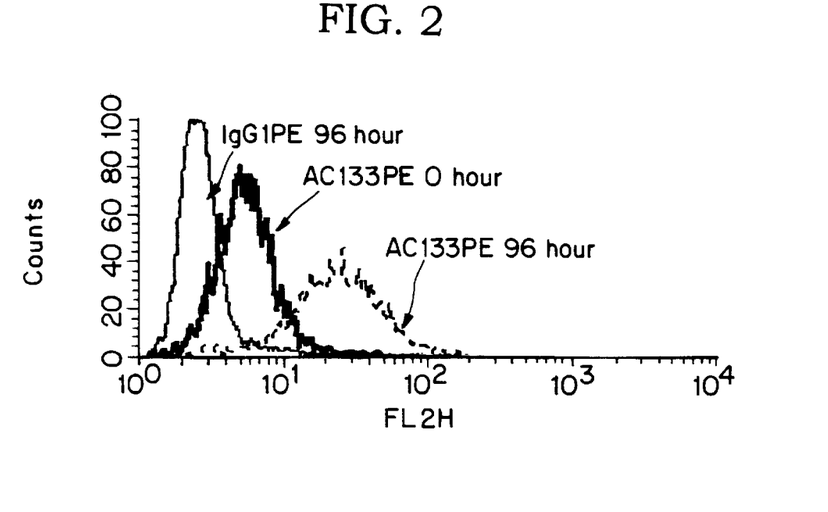
FIG. 2 is a graph showing FACS analysis of AC133 antigen expression on phorbol myristate acetate (PMA) activated Y79.1 cells.
Figure 3:
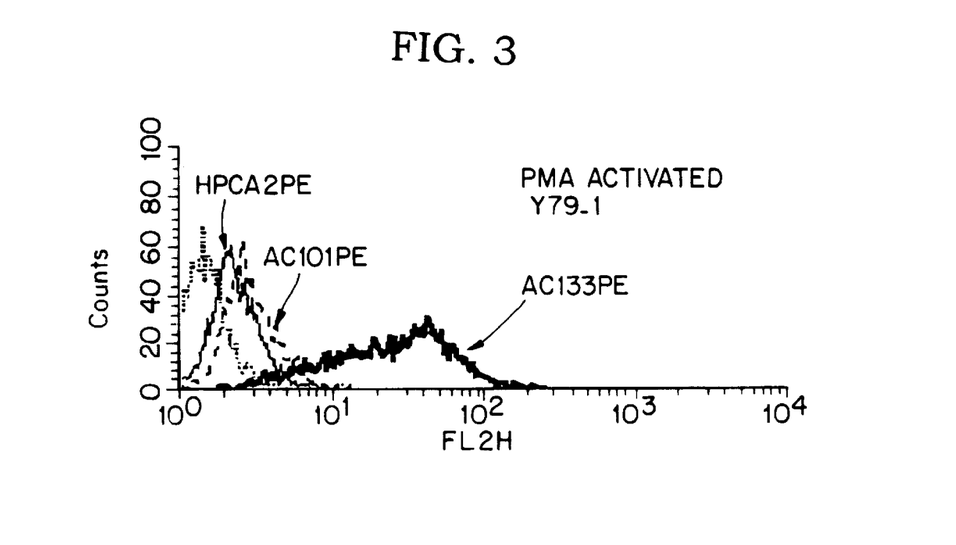
FIG. 3 is a graph showing FACS analysis of AC133 antigen and CD34 expression on PMA activated Y79.1 cells.

Activation of Y79.1 cells with PMA was found to increase the expression of AC133 antigen (shown in FIG. 2). However, PMA activation of several other cell lines, or PHA activation of human PBMC was unable to induce the expression of AC133 antigen (data are shown in Table 2). AC133 expression was not detectable on any of the $CD34^+$ cell lines tested. This finding, along with the lack of CD34 expression on the Y79.1 cell line (shown in FIG. 3), excludes the possibility that AC133 is directed to the CD34 antigen. AC133 expression is limited to human hematopoietic progenitor cells, unlike the CD34 antigen, which is also expressed on endothelium and fibroblasts (Krause et al. (1996) Blood 87:1–13).

AC133 is expressed on the $CD34^{bright}$ population of human progenitor cells isolated from fetal and adult bone marrow, fetal liver, cord blood, leukaphoresis (LP) packs and LP packs from cytokine mobilised donors. Typically it stains 30–50% of all $CD34^+$ cells in these populations.

TABLE 2

Activation of Cell Lines

Addition of PMA at 1 ng/ml for:

| | 0 hr | 24 hr | 48 hr | 72 hr | 96 hr | 144 hr |
| --- | --- | --- | --- | --- | --- | --- |
| Y79.1 | dim + | + | + | + | + | + |
| KG1a | – | – | – | – | – | N/A |
| K562 | – | – | – | – | – | N/A |
| HEL 92.1.7 | – | – | – | – | N/A | N/A |
| Jurkat | – | – | – | N/A | N/A | N/A |
| 8402 | – | N/A | N/A | – | N/A | N/A |

Addition of PWM at 10 μg/ml for:

| | 0 hr | 24 hr | 48 hr |
| --- | --- | --- | --- |
| Y79.1 | dim + | + | + |
| KG1a | – | – | – |

Figure 4A:
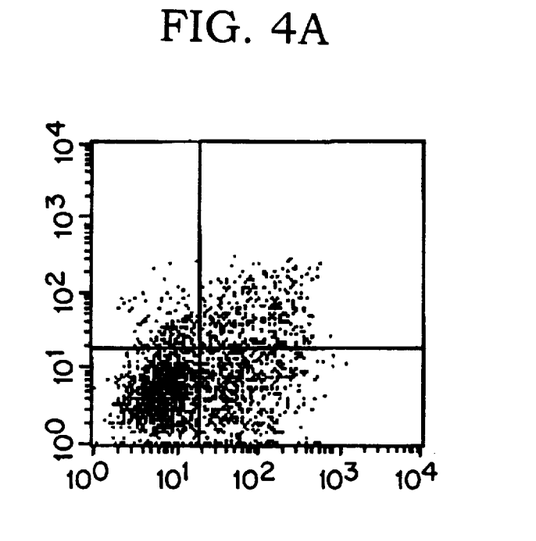
FIGS. 4A and 4B show dot-plots from 3 color FACS analysis of the antibodies AC133, CD38 and HLA-DR on fetal liver cells. The x axis in FIG. 4A represents HLA-DR-FITC, and the y axis represents cell staining with AC133-PE. The x axis in FIG. 4B represents CD38-FITC, and the y axis represents cell staining with AC133-PE.
Figure 4B:
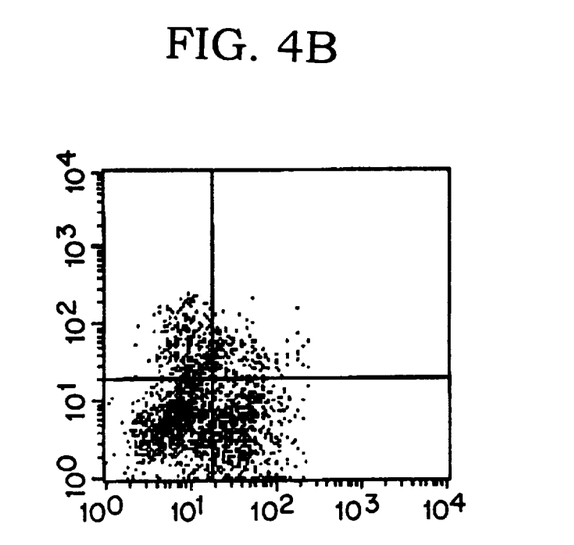
Figure 5A:
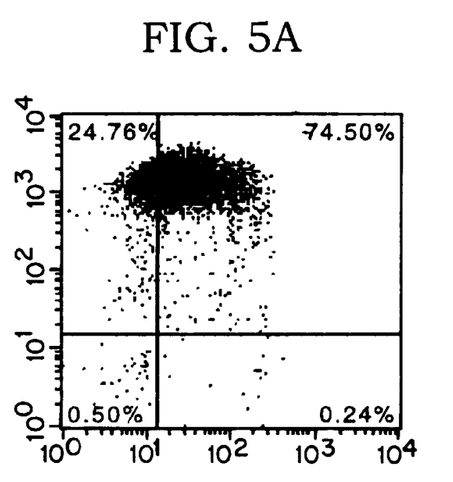
FIGS. 5A, 5B, 5C and 5D show dot-plots from FACS analysis of the antibodies CD38, HLA-DR, CDw90 and CD117 on AC133 positive cells purified from fetal liver.
Figure 5B:
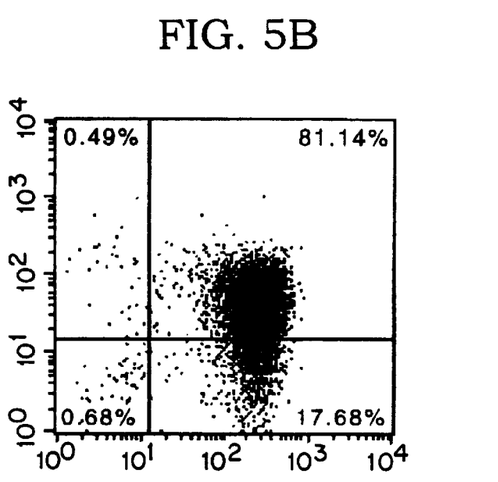
Figure 5C:
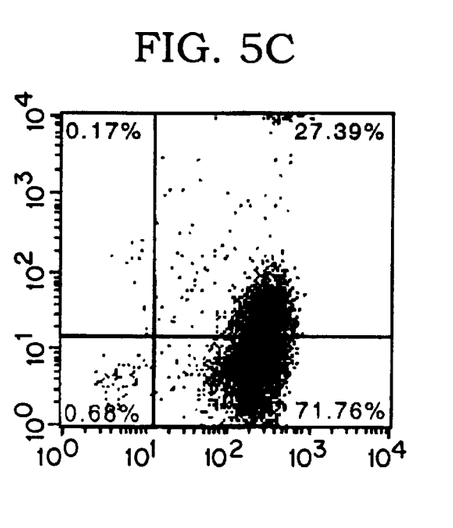
Figure 5D:
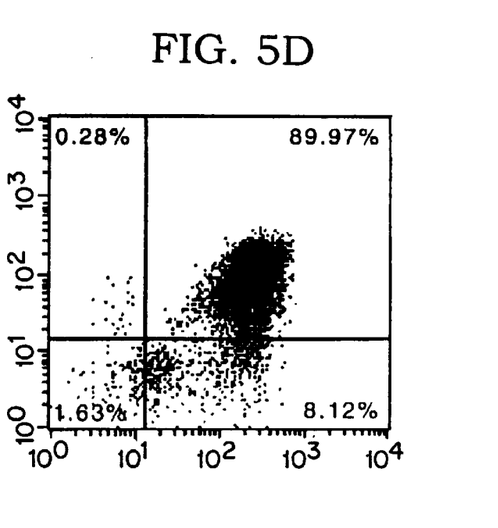

Phenotyping of AC133 positive cells. Phenotyping of AC133 and CD34 double positive cells was accomplished using 2 and 3 color FACS analysis, employing a panel of conjugated antibodies directed to cell surface structures known to be expressed on progenitor cells. Fetal liver, fetal and adult bone marrow, cord blood and peripheral blood were all used to determine the precise antigenic structure of AC133 positive cells. AC133 cells found in all of these tissues are $CD34^{bright}$, $CD38^{dim/neg}$ and $HLA-DR^+$. The data are shown in FIG. 4. The $CDw90(Thy1)^+$ and $CD117$ $(c-kit)^+$ stem cell populations are included within the AC133 positive population, as shown in FIG. 5.

In a series of experiments performed with AC133 immunomagnetically purified fetal liver cells, CD38-FITC conjugated antibody stained 74.5% of the AC133 purified cells, while 24.8% were CD38 negative. As expected, HLA-DR stained the majority of the cells (81.14%). CDw90 is shown to stain 27.4% of the test cells, while CD117 stained 90%. It is generally believed that primitive (repopulating) hematopoietic stem cells have the phenotype of $CD34^{bright}$, $CD38^{dim/neg}$, $HLA-DR^+$, $CD117^{dim}$ and $CDw90^+$. Thus, the AC133 antibody recognizes a phenotypically important population of human hematopoietic progenitor cells.

Immunoprecipitation of the AC133 Antigen

Immunoprecipiation experiments showed that the AC133 antigen has a molecular weight of 127 kD. Biotin (Pierce) labeled, activated Y79.1 cells were solubilized with lysis buffer: 2.5% Brij (Sigma), 25 mM Tris-HCI, pH 8.0, 125 mM NaCI, 2.5 mM EDTA, 2.2 µg/ml Aprotinin (Sigma) and 1 mM PMSF (Sigma). The lysates were incubated with AC133 and control antibodies after preclearing. Immunocomplexes were collected on Staphylococcus aureus cells (CalBiochem) and heated for five minutes at 95° C. in SDS-PAGE sample buffer with 1% 2-mercaptoethanol. Immunoprecipitates were resolved by SDS-PAGE and transferred to nitrocellulose membranes (Novex). Visualization was accomplished using streptavidin linked to horseradish peroxidase (HRP) (Amersham) and the Supersignal CL-HRP substrate system (Pierce). CD49d, CD71 and CD98 were used as controls, and their expected bands of 133 kD, 92 kD and 80/40 kD were observed in the corresponding lanes. The immunoprecipitation with AC133 showed a distinct band corresponding to a molecular weight of 127 kD. This band was absent in the samples that were immunoprecipitated with the anti-CD34 antibodies AC101, HPCA1 and HPCA2, indicating that CD34 is not expressed in the Y79.1 cell line. This is consistent with the FACs data.

The data from a further experiment using biotin labeled Y79.1, as well as KG1a cells, confirmed the AC133 molecular weight data by comparing CD34 and AC133 precipitates on the same gel. In this experiment, CD34 and Y79.1 antigens were precipitated from biotinylated KG1a ($CD34^+$) and Y79.1 lysates in adjacent lanes. The results clearly demonstrate that 1) each antibody precipitates its own distinct antigen, and 2) that the molecular weight of these two antigens is distinctly different, being 110 and 127 kD, respectively. Control experiments with HPCA2 and 16D11 (anti-CD34) precipitate a band of 110 kD from KG1a lysate, but do not precipitate anything from Y79.1 lysate. AC133 precipitates a 127 kD protein from the Y79.1 lysate, but nothing from the KG1a lysate. When KG1a and Y79.1 lysates were mixed, AC133 Ag and CD34 were co-precipitated. The results show that the two antigens are of different molecular weights.

Characterization of the AC133 Epitope

Figure 6A:
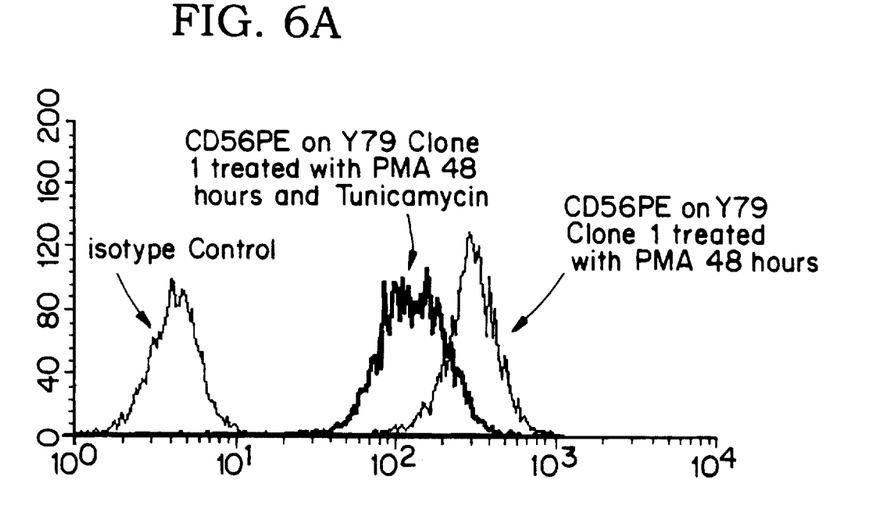
FIGS. 6A and 6B are graphs showing FACS analysis of CD56 (FIG. 6A) and AC133 antigen (FIG. 6B) expression on PMA activated, tunicamycin treated or untreated Y79.1 cells.
Figure 6B:
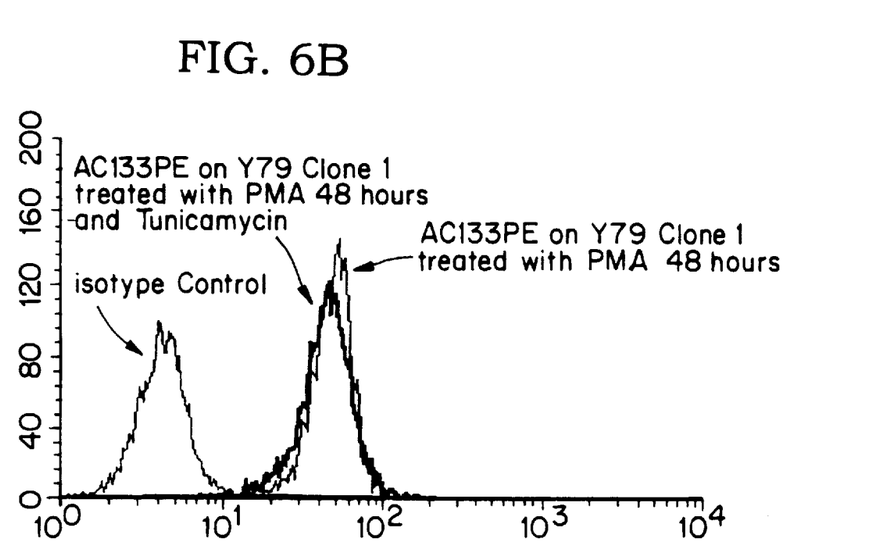

Y79.1 cells were activated for 48 hours with 1.0 ng/ml PMA, and then for a further 36 hours in the presence or absence of 2 µg/ml of tunicamycin, which is known to interfere with cellular glycosylation processes (Andrew and Ross (1995) in *Leukocyte Typing V.* Schlossman et al. eds. Oxford University Press. pp.591–592). The cells were then stained using a panel of known positive antibodies, including AC133. The results of this experiment are shown in FIG. 6. The CD56 intensity in panel (A) was shown to be markedly reduced, confirming that the tunicamycin treatment was effective. The staining of AC133 in panel (B) was unchanged by this treatment. In other experiments, AC133 was shown to react with neuraminidase treated Y79.1 cells. These results demonstrate that the AC133 antigen is a protein epitope, and that binding of the AC133 antibody is not dependent on glycosylation of the antigen.

AC133 Magnetic Bead Conjugation

Purified AC133 antibody was conjugated to magnetic amino-dextran beads using a standard protocol for 4-(N-maleimidomethyl)-cyclohexane-1-carboxylic acid N-hydroxysuccinimide ester (SMCC). AC133 antibody was added to SMCC activated beads at 5 µg per $OD_{450}$ unit, and incubated at room temperature for two hours. The reaction was stopped by the addition of β-mercaptoethanol and NEM. The conjugate was purified over two columns in the presence of a magnetic field, and eluted. The concentration was adjusted to $OD_{450}=10$, and OPG was added for stabilization. The conjugate in PBS and 0.1% sodium azide was filtered through a 0.2 µm filter, and stored at 4° C.

Figure 7:
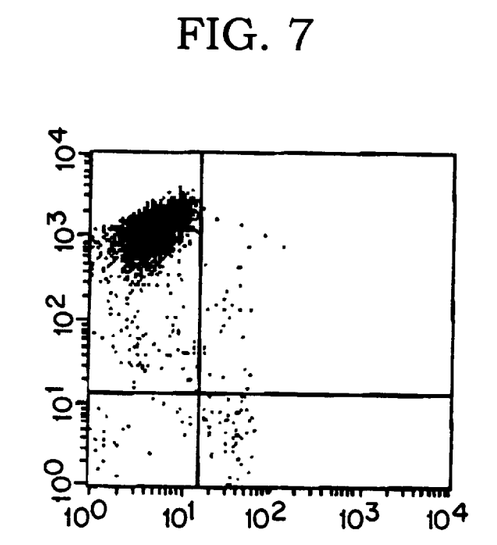
FIG. 7 is a dot-plot showing FACS analysis of HPCA2-PE (y axis) staining of AC133 magnetically purified fetal liver cells. The x axis represents staining with a glycophorin A-FITC conjugate.
Figure 8A:
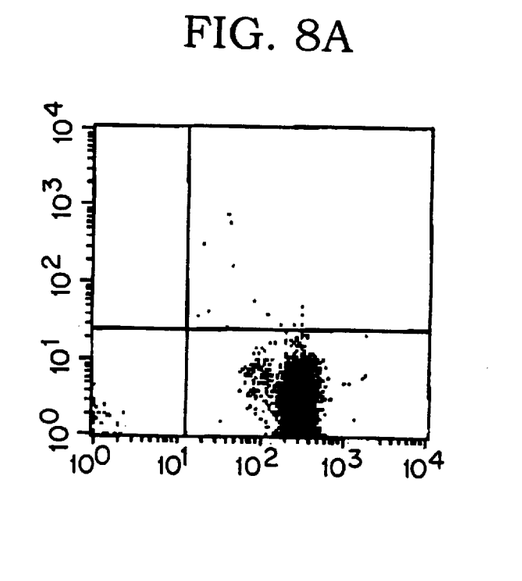
FIGS. 8A and 8B are dot plots showing FACS analysis of HCPA2 staining of buffy coat peripheral blood mononuclear cells before and after AC133 magnetic separation. The y axis shows staining with HCPA2-PE, the x axis shows staining with anti-CD45 and anti-CD15-FITC conjugated antibodies.
Figure 8B:
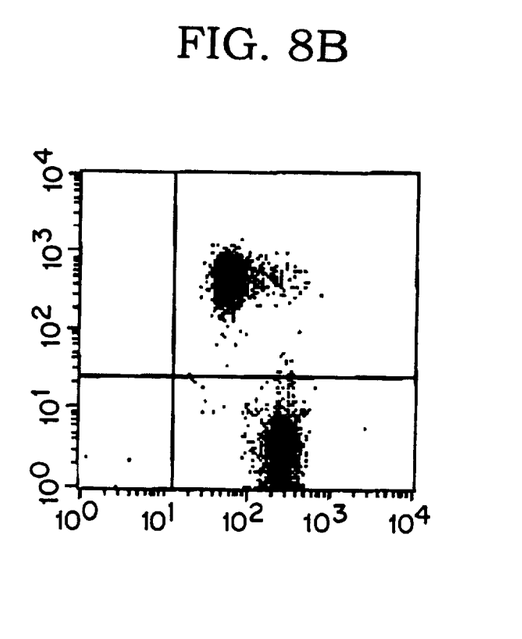

Separation of Human Hematopoietic Progenitor Cells with AC133 Magnetic Bead Conjugate AC133 direct magnetic bead conjugates were prepared and tested on buffy coat PBMCs, fetal liver WCI, fetal bone marrow and adult bone marrow. FIG. 7 shows the FACs dot plot of fetal liver cells purified with AC133 bead conjugte using the miniMACS system ands stained with glycophorin A-FITC and HCPA2-PE. The starting material contained 7.4% $CD34^+$cells, following AC133 purification, greater than 90% of AC133 purified cells were bright $CD34^+$. FIG. 8 shows that AC133 magnetic conjugate was also very effective in enriching $CD34^+$ cells from a buffy coat which contained about 0.26% $CD34^+$ cells. The final purified population was 64% positive for CD34, as shown by HPCA2-PE staining. This ability to separate cells in a magnetic purification system enables further study of the functional and phenotypic properties of AC133.

Clonogenic Potential of AC133 Positive Cells

Figure 9:
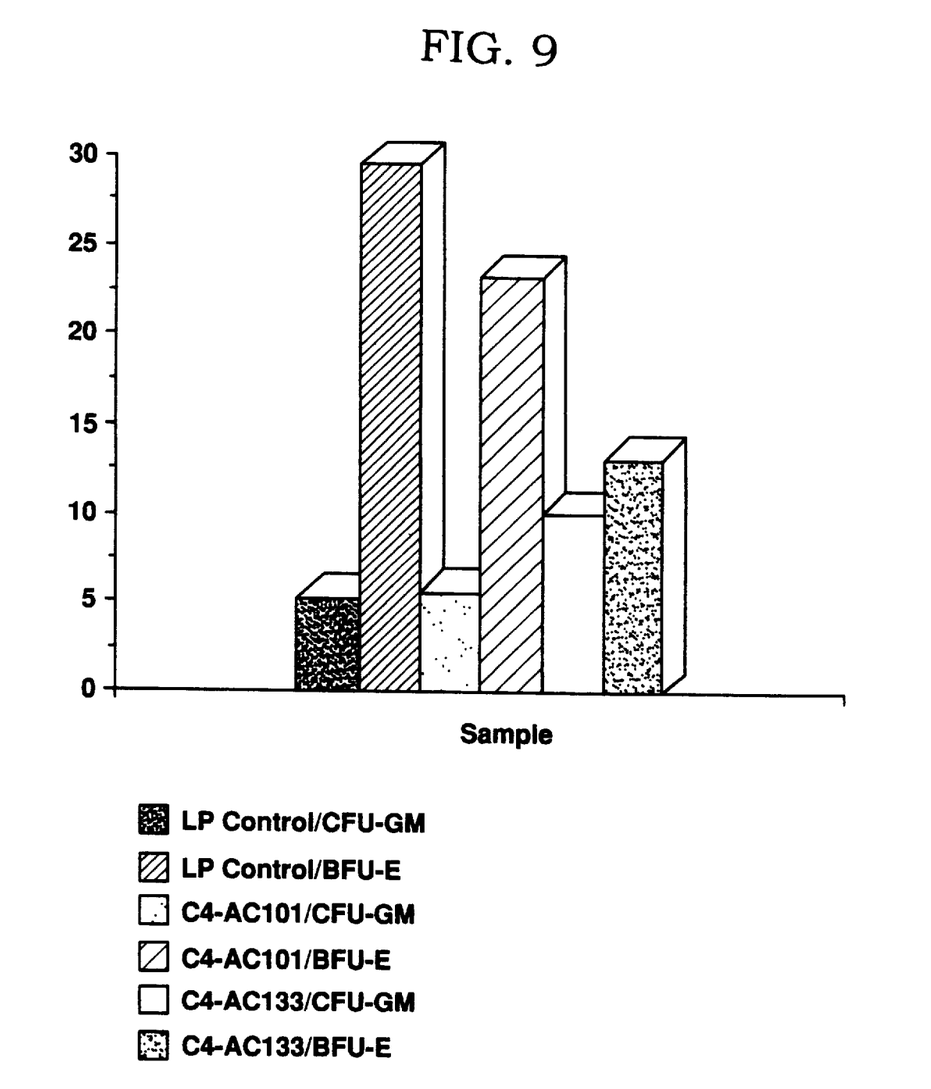
FIG. 9 is a bar graph showing the cloning efficiency of AC133 and HPCA2 purified cells in a clonogenicity assay.

AC133 magnetic beads selected cells purified from leukaphoresis packs were tested in clonogenicity assys using a commercially available kit (Stem Cell Technologies, Vancouver, B.C.). By providing a controlled growth environment utilizing recombinant human growth factors this culture assay identifies the major colony forming units (CFU) within a CD34 positive cell population. It provides information on the composition of progenitor cell populations, with respect to the relative percentages of cells committed to a particular lineage specific differentiation. Typically in peripheral blood derived $CD34^+$ cell populations BFU-e (burst forming units-erythroid), and CFU-GM (colony forming units-granulocyte macrophage) are the predominant colonies recognized, being present at a 3:1 ratio. FIG. 9 shows the results from a typical clonogenicity experiment comparing AC133 and CD34 purified cells obtained from a split leukaphresis pack. Colonies obtained with unfractionated control cells are typically predominantly BFU-E (29.34%), with a smaller number of CFU-GM (5.14%). CD34 purified cells show a similar distribution with 23.3% BFU-E, and 5.58% CFU-GM. In contrast, AC133 purified cells show a different pattern, with 13.1% BFU-E and 10.2% CFU-GM. Calculations show that 58% of CFU-GM were recovered in the AC133 purified fraction, while only 13% of BFUEs were recovered.

Figure 10:
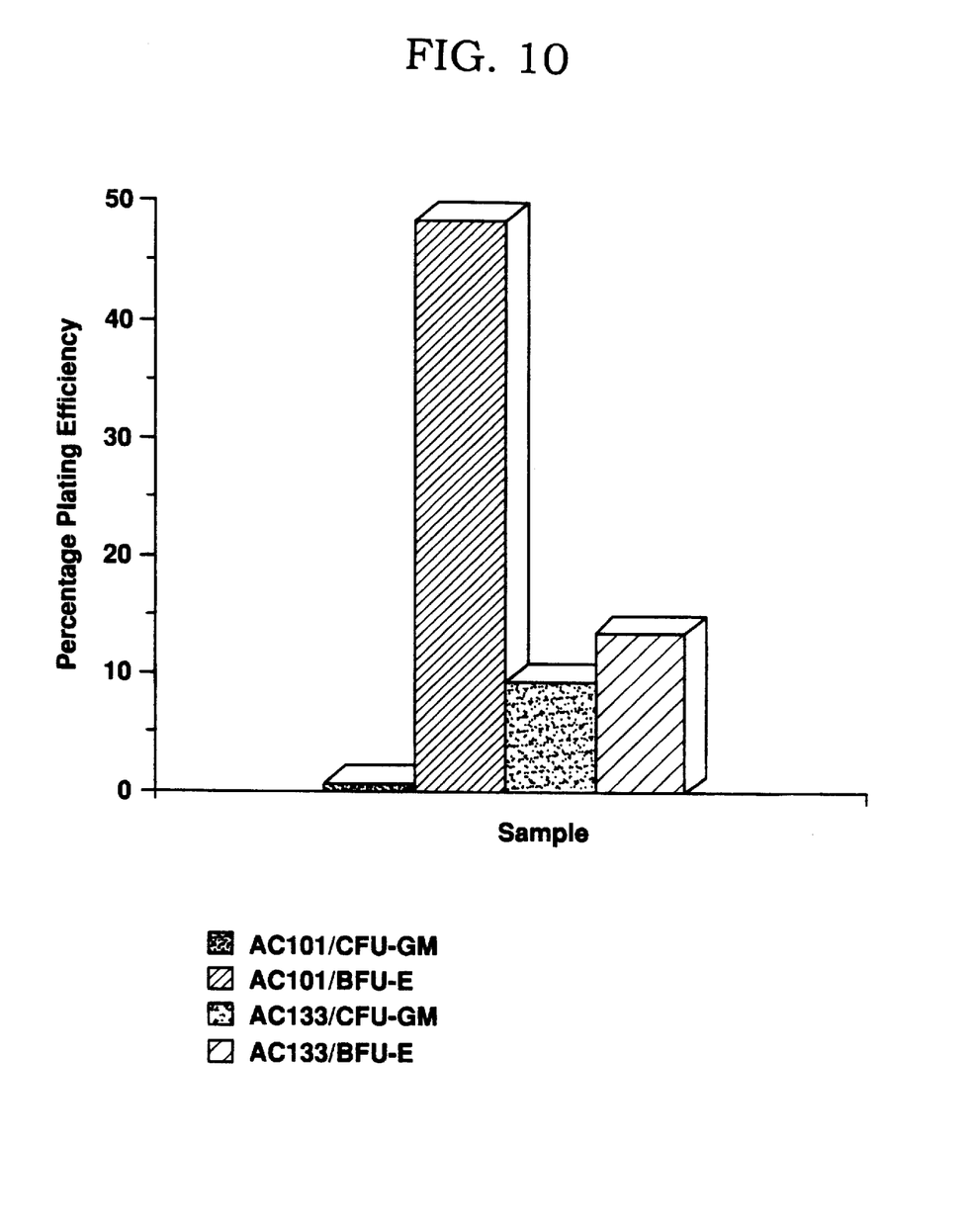
FIG. 10 is a bar graph showing the plating efficiency of AC133 purified cells and AC133 negative, CD34 positive cells.

FIG. 10 shows the results from a similar clonogenicity assay obtained following AC133 immunomagnetic purification. In this experiment, AC133 cells were positively selected, and then CD34 positive cells were positively selected from the AC133 negative flow-through. This design allowed the direct comparison of AC133$^+$ cells with CD34$^+$ but AC133$^-$ cells from the same donor. The results indicate that 93.8% of the CFU-GM progenitors were recovered in the AC133 positive fraction, the remaining 6.2% being recovered from the CD34$^+$/AC133$^-$ fraction. Conversely, the CD34$^+$AC133$^-$ fraction contained 78.0% of the BFU-e progenitors, while the remaining 22.0% were contained in the AC133$^+$ fraction.

The above experimental results rule out the possibility that AC133 is an antibody to Fc receptors, or that AC133 binds to stem cells via Fc receptor uptake. Further experiments rule out the possibility that AC133 staining is due to free PE. AC133 does not behave like an antibody to RTK, a receptor tyrosine kinase, TIE, a tyrosine kinase that contains immunoglobulin-like domains and growth factor homology domains and which is expressed in vascular endothelial cells and hematopoietic cells. AC133 does not behave like an antibody to P-glycoprotein, a 170 kD multi-drug resistance product which is also expressed inhematopoietic cells.

We have shown that AC133 recognizes an antigen expressed only on bright CD34$^+$ cells in bone marrow, fetal liver and peripheral blood. This antibody and its antigen do not match the molecular weight or distribution of any known CD antigen. Apart from stem cells, AC133 has been shown to react with a human retinoblastoma cell line that is negative for CD34 expresion. AC133 is, in addition, not expressed on a number of CD34$^+$ cell lines.

It is evident from the above results that the subject invention provides for a novel hematopoietic progenitor cell antigen, and antibodies that specifically bind to the antigen. Expression of the antigen is highly tissue specific. It is only detected on a subset of hematopoietic progenitor cells, and is present on substantially all cells that are active in the CFU-GM assay. This highly specific distribution of AC133 makes it exceptionally useful as a reagent for isolating and characterizing human hematopoietic progenitor and stem cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An antibody that specifically binds to the AC133 antigen, wherein said AC133 antigen specifically binds to the antibody produced by the hybridoma cell line ATCC HB 12346.

2. An antibody according to claim 1, wherein said antibody is a monoclonal antibody, produced by a hybridoma cell line.

3. An antibody according to claim 2, wherein said monoclonal antibody blocks simultaneous binding to said AC133 antigen by the antibody produced by the hybridoma cell line ATCCHB12346.

4. An antibody according to claim 1, wherein said antibody was raised through contralateral immunization.

5. A monoclonal antibody produced by the hybridoma cell line ATCCHB12346.

6. A method for enrichment of hematopoietic progenitor cells, said method comprising:

combining a mixed population of human cells comprising hematopoietic progenitor cells with a reagent that specifically binds to the AC133 antigen; and selecting for those cells that are AC133 positive;

wherein said selected cells are enriched in hematopoietic progenitor cell activity.

7. A method according to claim 6, further comprising:

combining said mixed population of human cells or said selected cell with reagents that specifically recognize at least one of the cell surface markers CDw90, CD117 and HLA-DR; and selecting for those cells that are positive for said at least one cell surface marker.

8. A method according to claim 5 or 7, wherein said reagent or reagents are antibodies.

9. A method according to claim 8, wherein at least one of said antibodies is fluorochrome conjugated.

10. A method according to claim 9, wherein said selecting with said fluorochrome conjugated antibodies is by flow cytometry.

11. A method according to claim 8, wherein at least one of said antibodies is conjugated to magnetic particles.

12. A method according to claim 11, wherein said selecting with said magnetic particle conjugated antibodies is by high gradient magnetic selection.

* * * * *